United States Patent [19]

Yoo et al.

[11] Patent Number: 5,140,463
[45] Date of Patent: Aug. 18, 1992

[54] METHOD AND APPARATUS FOR IMPROVING THE SIGNAL TO NOISE RATIO OF AN IMAGE FORMED OF AN OBJECT HIDDEN IN OR BEHIND A SEMI-OPAQUE RANDOM MEDIA

[76] Inventors: Kwong M. Yoo, 610 W. 141 St., Apt. 5J, New York, N.Y. 10031; Robert R. Alfano, 3777 Independence Ave., Bronx, N.Y. 10463

[21] Appl. No.: 489,942

[22] Filed: Mar. 8, 1990

[51] Int. Cl.⁵ .................... G02B 27/00; G01N 21/00; H04N 7/00; G21K 1/00
[52] U.S. Cl. .................... 359/559; 356/337; 358/95; 378/154
[58] Field of Search .......... 250/486.1, 363.02, 432 R, 250/432 PD; 364/413.19, 413.13; 356/338, 339, 336, 337; 378/99, 154, 37; 73/603; 350/171, 162.12; 358/95, 110, 111; 359/497, 498

[56] References Cited

U.S. PATENT DOCUMENTS

| | | | |
|---|---|---|---|
| 4,203,037 | 5/1980 | Gur et al. | 378/37 |
| 4,493,096 | 1/1985 | Rieke | 378/99 |
| 4,707,128 | 11/1987 | Coles | 356/5 |
| 4,710,637 | 12/1987 | Luckey et al. | 250/486.1 |
| 4,875,227 | 10/1989 | Rossi et al. | 378/154 |

*Primary Examiner*—Bruce Y. Arnold
*Assistant Examiner*—James Phan
*Attorney, Agent, or Firm*—Kriegsman & Kriegsman

[57] ABSTRACT

The quality of image of an object hidden inside a highly scattering semi-opaque disordered medium is improved by using space gate imaging or time gate imaging or space time gate imaging. In space gate imaging, a small segment of the object is illuminated at a time. The scattered light is passed through a spatial noise filter. On the image plane, an aperture is open at the position of the image segment which correspond to the segment of the illuminated object. A full image is obtained by scanning the object segment by segment and simultaneously recording the signal at the corresponding image segment. In time gate imaging, the unscattered (i.e. ballistic) portion of the pulse which contains the information of the image is temporally separated from the other (i.e. scattered) portions which contains the noise using a ultrafast laser pulse and temporal gating devices. The technique is in space-time gate imaging, the two techniques are combined to produce an image with a much higher signal to noise ratio. The time separation between the ballistic and scattered light may be increased by increasing thickness of random medium or by introducing small scatters into the random medium so as to make the medium more random. The signal to noise ratio can also be increased by making the random medium less random (so that there will be less scattered light). In addition, the signal to noise ratio can be increased by introducing an absorbing dye into the medium or by using a wavelength for the light which is in the absorption spectrum of the random medium or by making the medium more ordered (i.e. less random) or by using a pair of parallel polarizers.

14 Claims, 14 Drawing Sheets

THE RATIO OF BALLICTIC TO DIFFUSIVE SCATTERED LIGHT INTENSITY AT VARIOUS DISTANCES (Z)-FROM THE LIGHT SOURCE. THE RATIO IS NORMALIZED TO ONE AT $z = l_1$

TABLE 9a      $l_1 = 100 \mu m$

| $z(\mu m)$ | RATIO |
|---|---|
| 100 | 1.0 |
| 300 | 0.23 |
| 600 | 0.07 |
| 900 | 0.07 |
| 1200 | 0.23 |
| 1500 | 2.54 |
| 1800 | $9.31 \times 10^1$ |
| 2100 | $1.13 \times 10^4$ |
| 2400 | $4.56 \times 10^6$ |
| 2700 | $6.11 \times 10^9$ |
| 3000 | $2.72 \times 10^{14}$ |
| 3300 | $4.01 \times 10^{17}$ |
| 3600 | $1.97 \times 10^{22}$ |

TABLE 9b      $l_1 = 1000 \mu m$

| $z(\mu m)$ | RATIO |
|---|---|
| 1000 | 1.00 |
| 2000 | 2.72 |
| 3000 | $2.80 \times 10^1$ |
| 4000 | $1.10 \times 10^3$ |
| 5000 | $1.63 \times 10^5$ |
| 6000 | $9.16 \times 10^9$ |
| 7000 | $1.96 \times 10^{11}$ |
| 8000 | $1.59 \times 10^{15}$ |
| 9000 | $4.88 \times 10^{19}$ |
| 10000 | $5.69 \times 10^{24}$ |
| 11000 | $2.52 \times 10^{30}$ |

FIG. 9

METHOD AND APPARATUS FOR IMPROVING THE SIGNAL TO NOISE RATIO OF AN IMAGE FORMED OF AN OBJECT HIDDEN IN OR BEHIND A SEMI-OPAQUE RANDOM MEDIA

BACKGROUND OF THE INVENTION

The present invention relates generally to imaging objects and more particularly to a method and apparatus for improving the signal to noise ratio of an image formed of an object hidden in or behind a semi-opaque random media, the object being either opaque, transparent or semi-transparent.

Many objects that we wish to observe are hidden inside or behind some kind of semi-opaque random media. Some examples are tumors inside a breast, defects in a semiconductor, objects in the ocean or in a cloud or in smoke. The above are applications in medicine, electronics, military, and commercial fields.

When a light pulse propagates through a random medium, some of the light is multiply scattered. The multiple scattering of light reduces the intensity of the signal and increases the noise on the signal arising from the randomly scattered light. The reduction in signal and increase in noise from multiple scattered light are the main reasons why one cannot see through an optically thick random medium. Thus, one has to reduce the scattered light noise in order to enhance the quality of the image.

The following references are pertinent to the invention: An article entitled Simulation of Laser Tomoscopy In A Heterogeneous Biological Medium, J. M. Maarek etc., Med & Bio. Eng. & Computer, Jul. 1986, pp. 407–414; U.S. Pat. No. 4,099,060; U.S. Pat. No. 4,203,037; U.S. Pat. No. 4,066,901; U.S. Pat. No. 4,207,892; U.S. Pat. No. 4,515,165; U.S. Pat. No. 4,570,638; and U.S. Pat. No. 4,212,306.

It is an object of this invention to provide a new and improved technique for improving the signal to noise ratio of an image formed of an object hidden in or behind a semi-opaque random media.

SUMMARY OF THE INVENTION

According to one aspect of this invention, the quality of an image formed of an object, the object being either opaque, transparent or semi-transparent, that is hidden inside or behind a highly scattering semi-opaque disordered medium is improved by using space gate imaging or time gate imaging or space time gate imaging. In space gate imaging, a small segment of the object is illuminated at a time. The scattered light is passed through a spatial noise filter. On the image plane, an aperture is open at the position of the image segment which corresponds to the segment of the illuminated object. A full image is obtained by scanning the object segment by segment and simultaneously recording the signal at the corresponding image segment. In time gate imaging, the unscattered (i.e. ballistic) portion of the pulse which contains the information of the object is temporally separated from the other (i.e. scattered) portions which contain the noise using an imaging system which includes a ultrafast laser pulse and temporal gating device. The concept of time gating is based on the principle that the unscattered (ballistic) portion of the light pulse travels straight through the medium, and arrives at an earlier time than those portions that are scattered away from the straight line and as a result travel through longer distances. A combination of space and time gate imaging, called space time gate imaging, eliminates most of the scattered light, producing as a result an image with a much higher signal to noise ratio. According to another aspect of the invention, further improvements can be achieved by increasing the time separation between the ballistic and scattered light. One way of achieving this is by increasing the thickness of random medium. Another way of achieving this is by introducing small scatterers into the random medium. Still another way of achieving this is by introducing an absorbing dye into the medium. A further way of achieving this is by using a wavelength for the light which is in the absorption spectrum of the random medium. The signal to noise ratio can also be improved by making the random medium either more random so as to increase the time separation between the scattered and unscattered and or by making the random medium more ordered so that less scattering will occur.

BRIEF DESCRIPTION OF THE DRAWINGS:

In the drawings wherein like references represent like parts:

FIGS. 9(a) and 9(b) are tables showing changes in the ratio of ballistic to diffuse intensity at various distances;

DETAILED DESCRIPTION OF PREFERRED EMBODIMENTS

Figure 1:
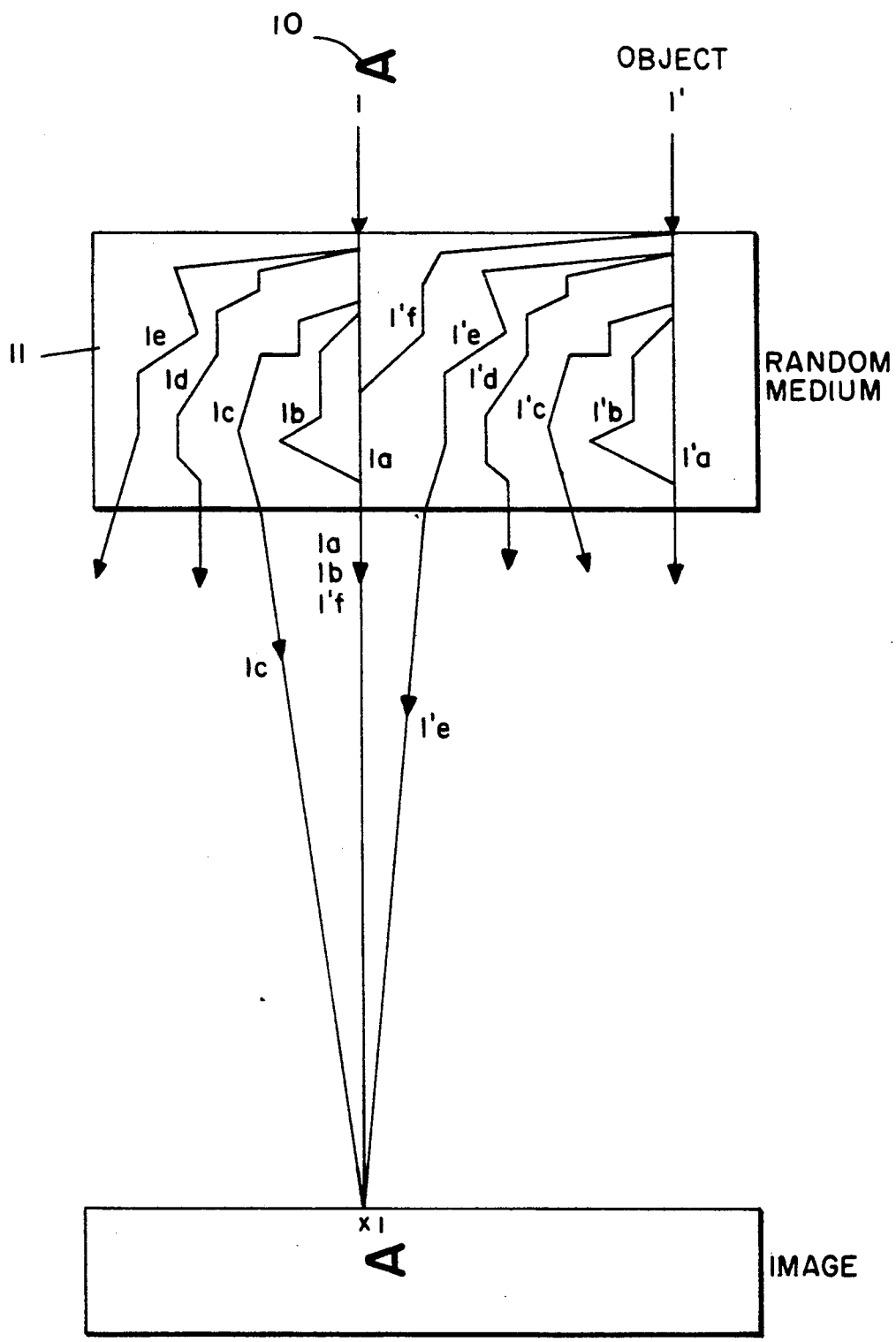
FIG. 1 is a schematic diagram showing the path of light through a random medium.

The sources of multiple scattered light noise in forming an image of an object 10 are classified and illustrated by rays in FIG. 1. The light from object 10 on passing through a random medium 11 may be divided into two portions, ray (1) and ray (1'). Ray (1') includes all incident rays except ray (1).

All the possible trajectories through the slab of random media may be grouped as follows:

a—unscattered light;
b—scattered away from the straight line path but scattered out of the medium along the same path as ray (a);
c—scatter and fall onto the position of $\vec{x_1}$;
d—scatter and come out propagating parallel to the ray (a);
e—all other scattered light; and
f—light scattered from the other ray and scattered out along the same path as ray (a).

Figure 2:
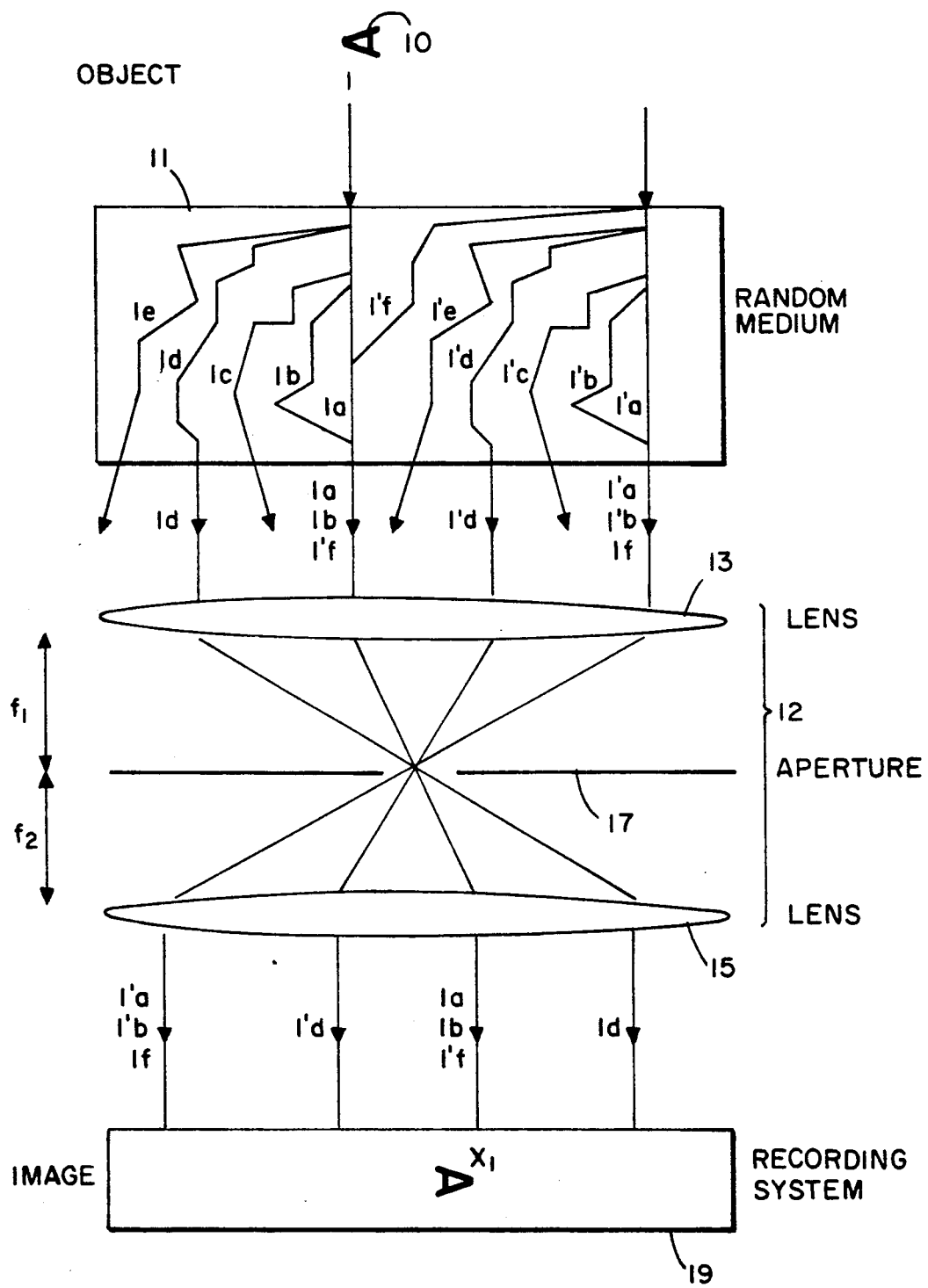
FIG. 2 is a schematic diagram of a spatial filter according to this invention.

If the object 10 is illuminated by a plane wave, then the dominant noise at $x_1$ comes from ray (1'e). To remove this noise, a spatial filter 12 which consists of a pair of lenses 13 and 15 and an aperture 17 placed at the focal point is used. This is shown in FIG. 2 where the light scattered away from the forward direction are removed and the image formed is recorded by a recording system 19. However, there are still two sources of noise which are rays (1'f) and (1b) at position $x_1$.

Figure 3:
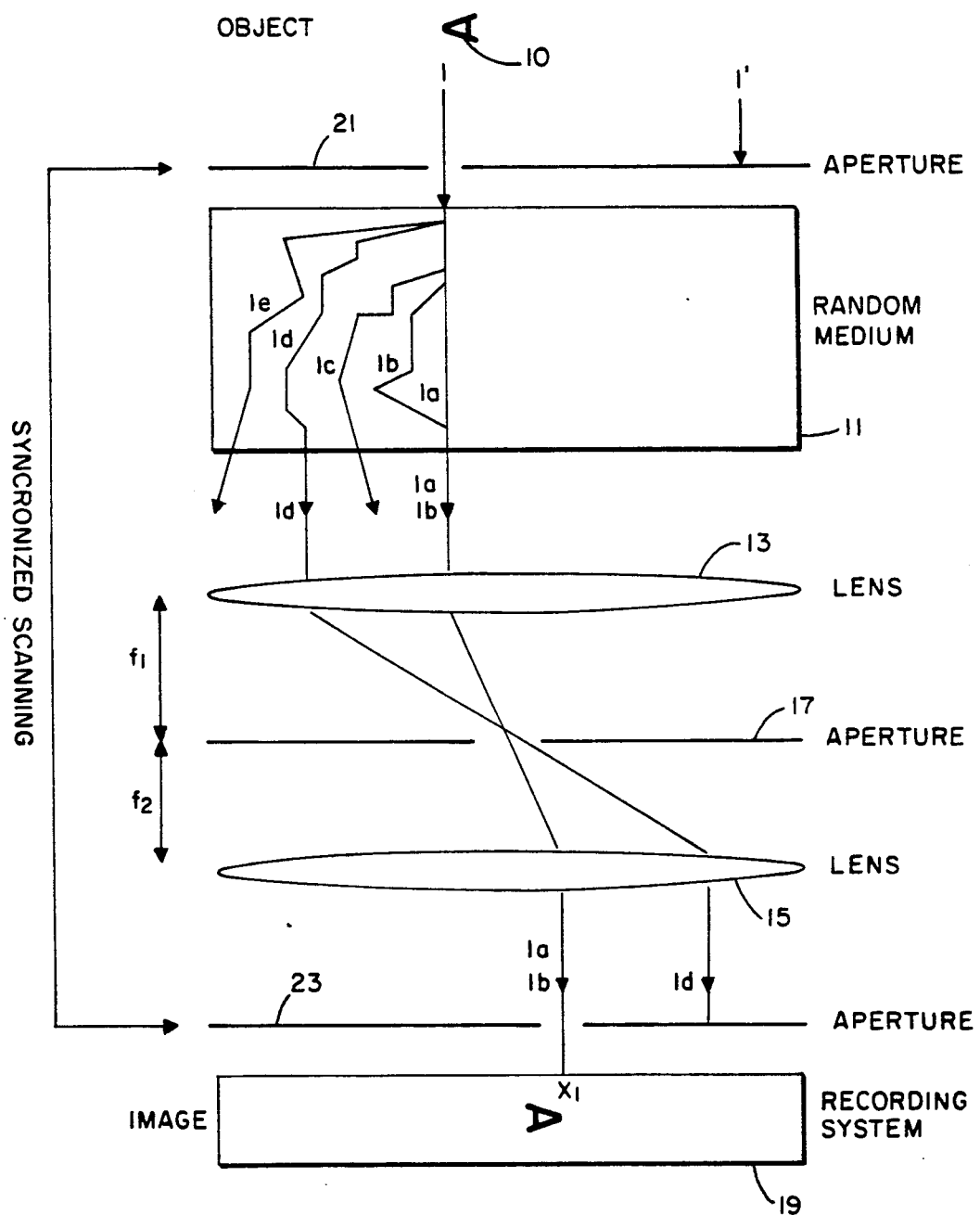
FIG. 3 is a schematic diagram of a space gate system according to this invention.
Figure 4:
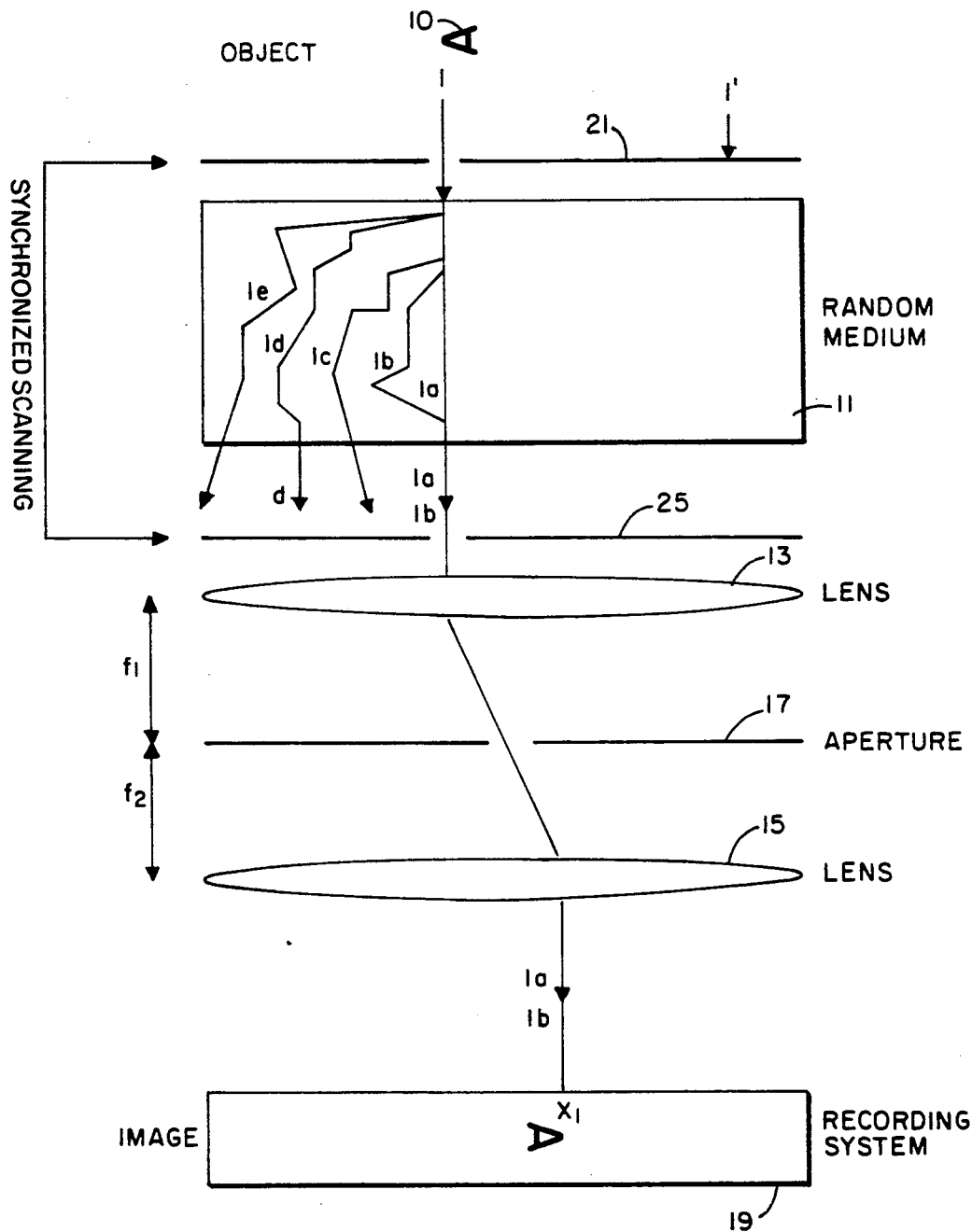
FIG. 4 is a schematic diagram of a variation of the system shown in FIG. 3.

In FIGS. 3 and 4 is shown an arrangement referred to as space gate imaging for removing the noise from rays (1') and (1d). The noise contribution from rays (1') is removed by blocking ray (1') itself so that it is not incident on the random medium. This elimination can be achieved either by placing an aperture 21 which allows only ray (1) through or just illuminates the medium by only ray (1). Multiple scattered light other than the forward direction of ray (1) is removed by the collimating lenses 13 and 15 and aperture 17 at the focal point. The noise of ray (1d) is removed either by placing an aperture 23 in front of the recording system as shown in FIG. 3 or by placing an aperture 25 in front of the collimating lenses 13 and 15 and aperture 17 as shown in FIG. 4. This reduction of unwanted multiple scattered light and some incident rays improves the quality of the image significantly. Nevertheless, the weakest noise represented by ray (1b) remains.

The fundamental principle of the space gate imaging is illuminating a small segment of the object, filtered out the multiple scattered light which scattered away from the forward direction, and the signal fall on the corresponding image position is recorded. The image is constructed after scanning the whole object segment by segment.

Figure 5:
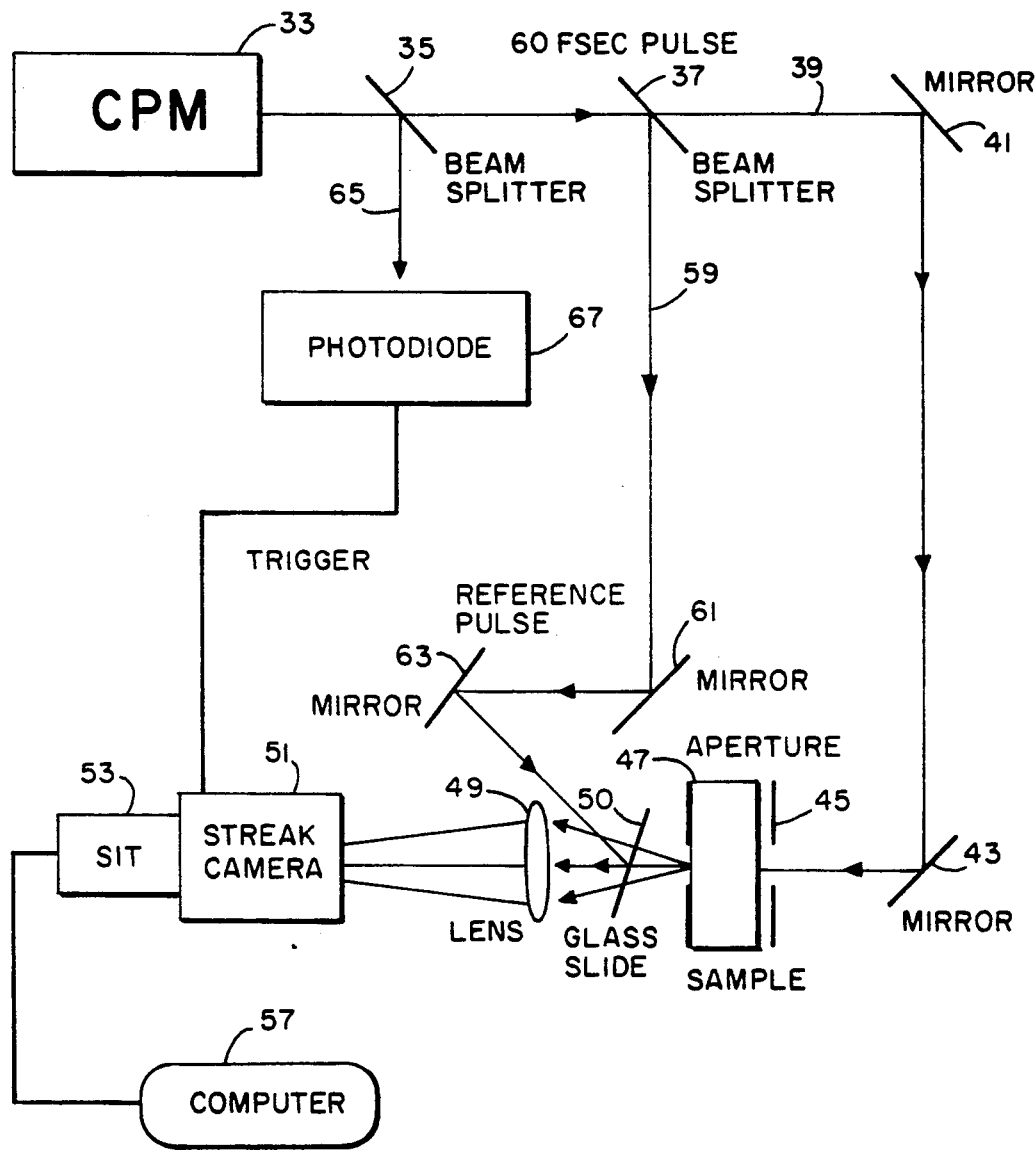
FIG. 5 is a schematic diagram of an experimental apparatus used to study the angular and temporal distributions of an ultrafast laser pulse after propagating through a slab of a random medium.

In the space gate imaging system described above, the noise represented by ray (1b) cannot be removed. This noise can be significant in a strongly scattering medium. To illustrate this, the relative intensity between ray (1a) and (1b) are time resolved. The experiment setup is shown in apparatus 31 in FIG. 5 and the measured results are presented by two pictures in FIGS. 6(a) and 6(b). In apparatus 31, a beam of pulses from a colliding pulse mode locked laser 33 is split into three parts by a pair of beamsplitters 35 and 37. One part 39 is deflected off a pair of mirrors 41 and 43 and then passed through an aperture 45 and a sample 47 and then imaged by a lens 49 through a beamsplitter 50 into the input end of a streak camera 51. The streak image formed at the output end is converted into an electrical signal by a silicon intensified target (SIT) detector 53 and then fed into a computer 57. Another part 59 of the beam from laser 33 is deflected off a pair of mirrors 61 and 63 and used as a reference pulse for streak camera 51. The third part 65 of the pulse from laser 33 strikes a photodiode 67 and generates a trigger signal which is used to trigger the deflection circuits (not shown) in streak camera 51. The degree of whiteness in the two pictures measure the intensity of the light falling on the picture. The horizontal and vertical axis are angle and time axis, respectively. A small white spot corresponds to the signal from ray (1a). The broad white distribution correspond to the scattered signals which has large time and angular distributions. The intensity of the light scattered in the forward direction (angle=0 mrad) in time is traced by a white line in the picture. The first peak is the reference pulse, the second peak is the ballistic pulse (ray (1a)), and the broad distribution in angle and time corresponds to the scattered pulse (ray (1b)). The time integrated intensity of ray (1b) can be greater than the ballistic portion (1a). This large noise from ray (1b) will overshadow the image in space gating imaging. Time gating can select ray (1a) more and enhances the image quality.

Since the signal and noise arrive at different times, one may temporally (i.e. time) gate and record only the ballistic portion of the pulse as the signal. This separation can be easily accomplished with present streak camera technology and nonlinear optical methods. Thus, the noise represented by ray (1b) can be reduced substantially.

Space-time gate imaging is similar to space gate imaging (FIGS. 3 and 4) except that the recording system of the space-time gate imaging temporally gates the signal component of the scattered light. The leading edge of the light pulse, which consists of mainly the signal (1a) is measured. This will substantially improved the quality of the image.

The above two principles eliminate some (space gating) or most (space-time gating) of the possible noise from the scattered light and thereby improve the quality of the image. A complete imaging system requires several additional steps to be taken in succession. First, a small segment of the object is illuminated and the signal light falling on the corresponding image position on the image plane is detected and stored and then recorded after passing though a space gate filter. This signal is stored in the memory in a computer. The whole object is scanned segment by segment and the signal at the corresponding segment on the image plane is recorded and stored. This scanning can be done by moving the object alone, or optical deflection by acoustic modulation, or by synchronizing the motion of illumination spot and detecting spot. The image is then reconstructed from all the stored signals and the picture is shown on the video screen. The picture can further be used for analysis and diagnosis such as by comparing the images in the memory of the computer.

Figure 7:
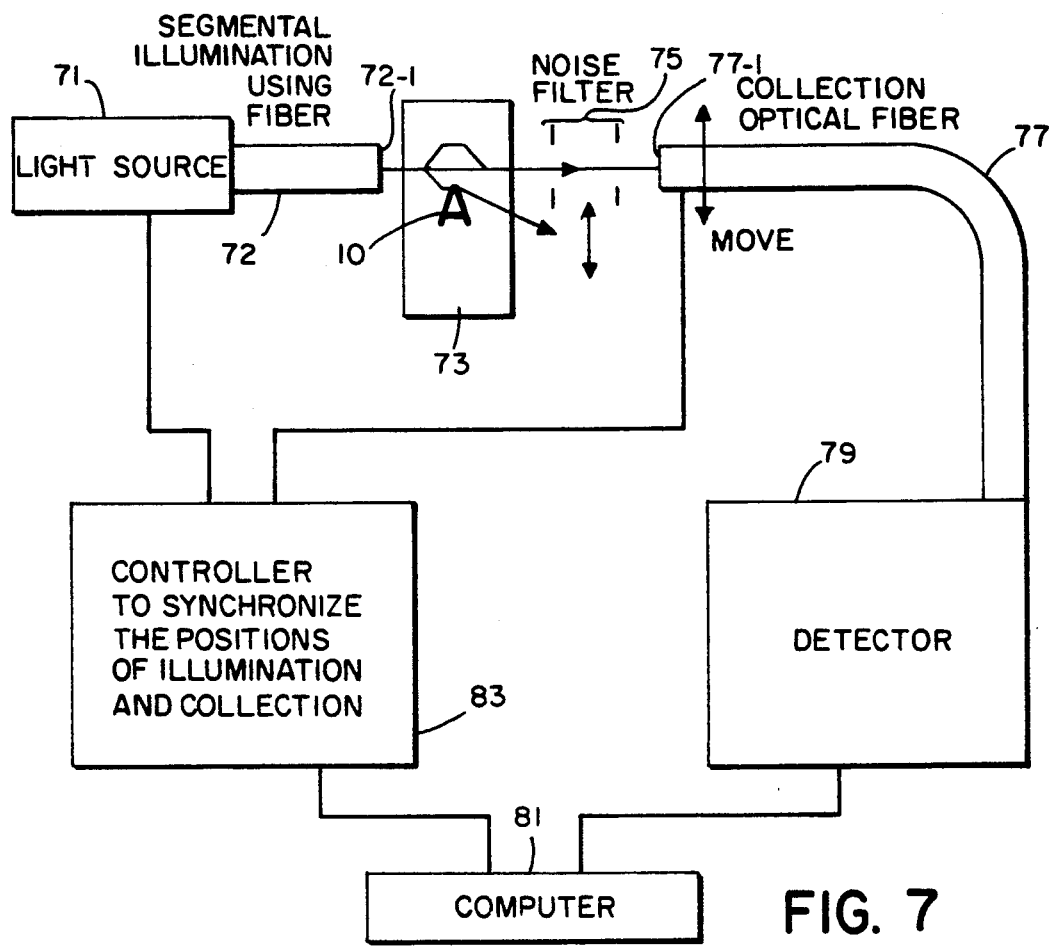
FIG. 7 is a block diagram of an imaging system according to this invention.

A block diagram shown in FIG. 7 illustrates one of the typical imaging systems taught by our invention. A cw or ultrafast laser pulse is generated from a laser light source 71 and outputted through a fiber 72 and incident on the medium 73 in which an object 10 is hidden. The multiple scattered light strikes a noise filter 75 of the type described in FIGS. 3 and 4. An optical fiber 77 is used to collect the unscattered (ballistic) and scattered light. The collection fiber 77 is placed at the image point which corresponds to the illuminated point on the object, and the signal is collected and guided to a detector 79 the output end 72-1 of fiber 72 and the input end 77-1 of fiber 79 constitute a space gate. To obtain the complete image of object 10, one has to move and scan the whole object 10 point by point and move the optical fiber 77 as shown by arrow D so that the corresponding signal on the image point is collected. Light source 71 and fiber 77 are synchronized in positions of illumination and collection by a controller 83 which is is monitored by computer in a computerized recording system 81 so that the correlation between the position of illumination on the object 10 and the signal collected is established. An acoustic optical deflection modulator (not shown) can also be used to deflect the beams to different locations on objects. Also, a selected portion can be collected and deflected by another acoustic optical deflector. This is similar to a bar code reader. The scanning can also be done by translating the position of object 10 alone. Three dimensional information of object 10 can be obtained by an additional degree of scanning such as rotating the object. The signal collected by the optical fiber 77 is sent into a detector system where the intensity is measured and stored into computer in system 81.

Detector 79 may comprise, for example, a photomultiplier tube or a streak camera coupled to an SIT or video camera or a Kerr cell coupled to an SIT or a video camera.

If detector 79 is a photomultiplier tube or the equivalent, then the system is a space gate type of system. On the other hand, if the detector is a streak camera combination or a Kerr cell combination or similar combination, then the system is a space gate, time gate type of system. The output of detector system 79 is fed into a computer 81 for processing and recording. Computer 81 and light source 71 are controlled by controller 83 which receives instructions from computer 81. A complete image can be reconstructed after a full scan or many full scans.

Figure 8:
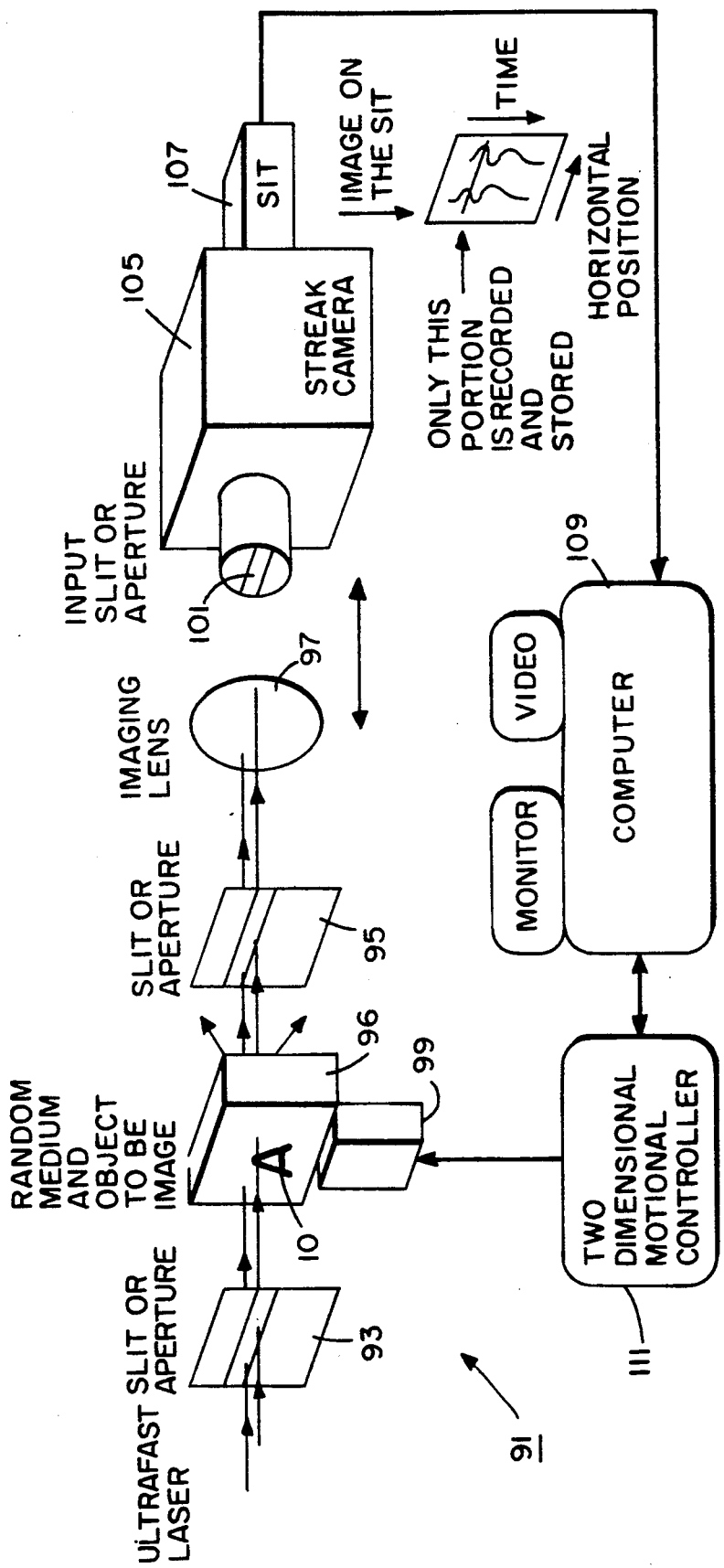
FIG. 8 is a diagram of a space-time gate imaging system coupled directly with a streak camera system.

Another versatile space-time imaging system 91 which incorporates a streak camera is shown in FIG. 8. The system includes two slits (or apertures) 93 and 95 a semi-opaque random medium, a lens 97, and a translation stage 99. Slits 93 and 95 and an imaging lens 97 comprise a space gating device where all the light scattered away from the straight line propagation is cut off by the input slit or the aperture 101 of a streak camera 105. The object 10 inside random medium 96 is illuminated by ultrafast laser pulses. The scattered light is temporally dispersed by streak camera 105. The output streak image is converted into an electrical signal by SIT 107 and fed into a computer 109. Stage 99 is controlled by controller 111 which is controlled by computer 109. Only the front portion of the transmitted pulse which corresponds to the unscattered signal is recorded in computer 109. Then the next line or point segment of object 10 is illuminated, which can be done either by moving random medium 96 or apertures 93 and 95. An acoustic optical deflector (not shown) can be incorporated and used to map out the object. The ballistic signal is again measured and stored in computer 109. The computer software correlates the recorded signal and the illuminated segment of the object. After a full scan, the image is reconstructed from the computer software.

The resolution of the image formed by the ballistic component of the pulse is governed by wave diffraction, i.e. the size of the apertures of illumination and collection and the wavelength of light. This resolution is the same as the resolution of usual imaging of an object without multiple light scattering. Using visible radiation, the resolution is in the order of micrometers. This resolution will make imaging of small particle possible. The diffusive component of the pulse may temporally overlap with the ballistic component within the time resolution of the detecting system. This overlapping increases the noise and reduces the resolution of the image. If the intensity of the diffusive component in the overlapping region is comparable to or larger than the ballistic component, the object may be deemed unobservable. The temporal separation between the diffusive component and the ballistic component can be increased by increasing the thickness of the media, increasing the number density of the scatterers, and decreasing the size of the scatterers or introducing particles smaller than the wavelength of the light into the random medium. Also, the quality can be improved by making the medium more random or less random (i.e. ordered). In these cases although the intensity of the ballistic pulse decreases the relative intensity of the ballistic to diffusive pulse within the time resolution increases. This increase in relative intensity enhances the quality of the image.

For some thin and lightly scattering random medium, the diffusive portion may temporally overlap with the ballistic portion of the pulse within the temporal resolution of the detecting system. This overlapping decreases the resolution of the image. To improve the image resolution to a microns scale one has to resolve the ballistic component from the diffusive component. This can be achieved by any of the ways as stated above:

The enhancement of image quality by increasing the medium thickness can be understood by looking at how the intensity for ballistic and diffusive components decrease with distance z from the source.

The intensity of the ballistic pulse is given by:

$$I_b(z) = e^{-z/l_t}\delta(+) \qquad (1)$$

where $l_t$ is the transport means free path.

The diffusive pulse is given by:

$$I_d(z) = \frac{1}{(4\pi Dt)^{3/2}} e^{-z^2/4Dt} \qquad (2)$$

where $D = vl_t/3$ is the diffusion coefficient, and v is the velocity of the light in the medium. Note, the intensity of the ballistic pulse decrease exponentially with distance (z), whereas the diffusive component decreases exponentially with square of the distance ($z^2$). Therefore, the diffusive intensity decreases faster than the ballistic intensity as the distance increases at a given time interval. Thus, the ratio of ballistic intensity to the diffusive intensity within the resolution time interval increases with increasing thickness. This large ratio $I_b/I_d$ enhances the image quality.

The change of ratio of ballistic to diffusive intensity ($I_b/I_d$) at various distances from the light source are illustrated by two examples. The results from two media with $l_t = 100\mu$ and 1000 $\mu$m are presented by tables displayed in FIG. 9. Since we are interested in the relative change in the ratio as the thickness (z) of the medium increases, the ratio is normalized to 1 when $z = l_t$. The diffusive intensity is the total time integrated intensity measured at the initial portion of the scattered pulse within the time resolution of the detector. The diffusive intensity may be presented by the value computed at time in the middle of the time resolution. The diffusive intensity is computed at $t = 5$ ps, which is at the middle of the 10 ps time resolution for a typical streak camera.

Table 9(a) tabulates the computed ratio ($I_b/I_d$) at various distances z for the case $l_t = 100$ $\mu$m. The ratio is equal to 1 when $z = 100\mu$. This is due to normalization of the ratio at $z = l_t = 100$ $\mu$m. As z increases, the ratio ($I_b/I_d$) decreases initially and then increase rapidly. This initial decrease in ratio can be understood by examining the exponential factor of the diffusion equation which is:

$$\frac{r^2}{4Dt} = \left(\frac{z}{4vt/3}\right)\left(\frac{z}{l_t}\right) \quad (3)$$

Note, ($z/l_t$) is scaled by a factor $z/(4vt/3)$. If this factor $z/(4vt/3)$ is less than 1, then the ratio can be less than one. The diffusive intensity increases faster than the ballistic intensity as z increase. For the ratio to increase with z, $z/(4vt/3)$ should be greater than one. The critical value for z is:

$$z_c = 4vt/3 \quad (4)$$

If $z > z_c$, the ratio of ballistic to diffusive intensity will increase with increase z. As an example presented in table (1a), $t = 5$ ps, and v is the light velocity in water, then $z_c = 1500$ $\mu$m. This critical value is in agreement with the computed data in table 9(a) for $z < 500$ $\mu$m the ratio is less than 1; for $z > 1500$ $\mu$m the ratio increase rapidly with z.

Table 9(b) illustrates another example for $l_1 = 1000$ $\mu$m. The ratio increase rapidly with distance z. These illustrations mean that the ballistic intensity may be increased with respect to diffusive intensity by introducing a slab of random medium with thickness greater than $z_c$ between the object to be imaged and the detector.

Figure 6B:
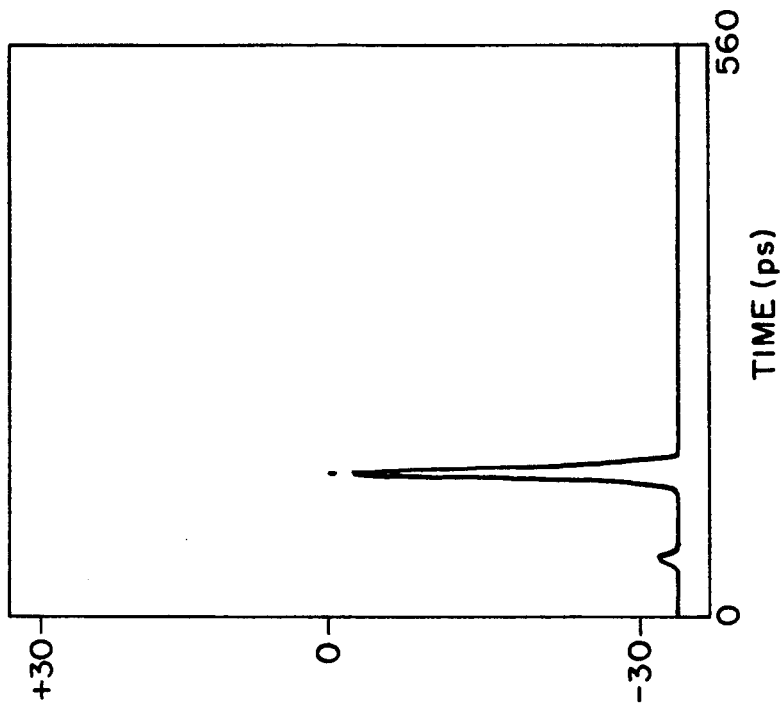
FIGS. 6 (a) and (b) are graphs of the angular and temporal behavior, respectively, of a light pulse propagating through a 10 mm slab of a random medium using the experimental apparatus of FIG. 5. Photographs are taken by a streak camera which displays both the angular and temporal information of the scattered lights. The first white spot is from the prepulse, the second spot is the coherent component, and the incoherent component is spread over a wide angular and temporal region. The curve traces the intensity versus time for waves scattered in the forward direction $\pm 1$ mrad. The random media consist of latex beads suspended in water, Picture (a), $d=0.33$ $\mu$m, number density $n=9.5\times 10^{16}$ m$^{-3}$, $n\sigma_s z=24$; Picture (b), $d=15.8$ $\mu$m, $n=4.7\times 10^{12}$m$^{-3}$, $n\sigma_s z=19$.
Figure 6A:
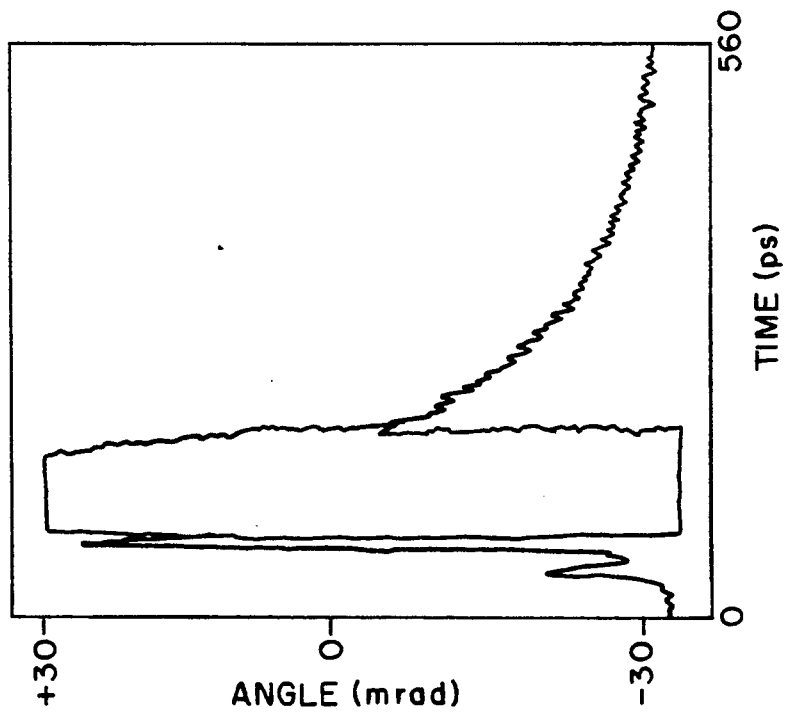

The effect of adding small particles on the pulse profile is best understood by two pictures displayed in FIGS. 6(a) and 6(b) which show the angular and temporal information of the pulse after propagating through a 10 mm slab of random media. The random media consists of latex beads suspended in water. Picture (a) of FIG. 6 is for the case of latex beads with diameter of $d = 0.33$ $\mu$m which is small compared with the wavelength of the laser ($\lambda = 0.465$ $\mu$m) in water. Note, the ballistic pulse is clearly separated from the diffusive pulse in FIG. 6 (a). In contrast, the ballistic and diffusive pulses is not separated in picture (b) of FIG. 6 which is for the case of large diameter latex bead ($d = 15.8$ $\mu$m $> \lambda$). These pulses (ballistic and diffusive) fall together with 8 ps which is the resolution of the detecting system. The addition of small particles increase the time separation between the ballistic and diffusive pulse, and spectral resolution. One should expect by introducing smaller particles into a big particle medium, one would effectively increase the temporal separation between the ballistic and the diffusive pulses. This will enable us to measure the ballistic component better and give better imaging capability.

Figure 10A:
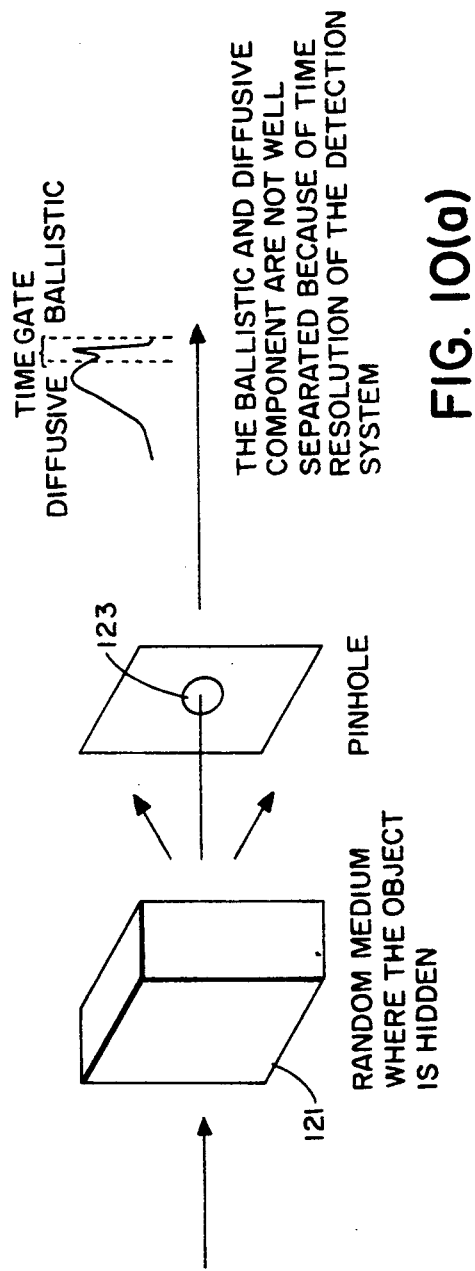
FIGS. 10(a) and 10(b) are schematics showing how a slab of random medium is introduced to increase the spatial resolution and to improve the signal to noise quality of the image.

FIG. 10(a) shows the effect of light passing through a random medium 121 and a pinhole 123.

Figure 10B:
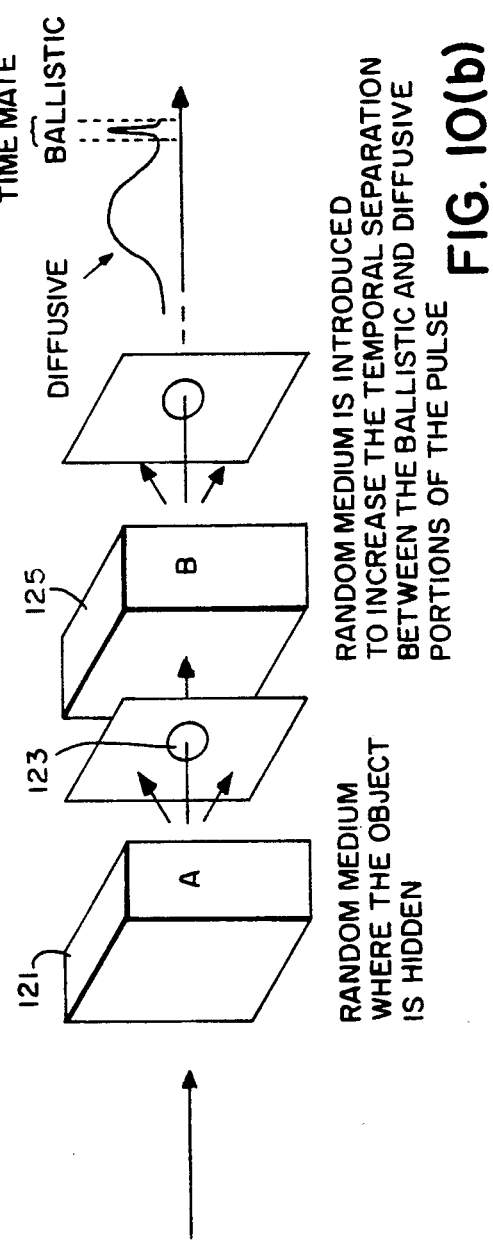

FIG. 10(b) shows the effect of introducing a slab 125 of uniform random medium of small particles into the path of scattered light from an object hidden (not shown) in a slab 121 to be image in order to increase (1) the temporal separation between the ballistic and diffusive pulse, and (2) the ratio of ballistic to diffusive intensity. This additional random medium delays the diffusive portion of the pulse with respect to the ballistic portion so that they can be further temporally separated within the resolution of the detecting system. The thickness of the slab should be greater than $z_c$. The slab should consist of scatterers much smaller than the wavelength of the light. The small scatterers scatter the light in all directions so as to increase the temporal separation between the diffusive and the ballistic pulse. This method will increase the temporal distance between the ballistic and diffusive parts so as to improve imaging capability. If the object is hidden inside a fluid type of medium, then the randomness of the media can be increased by introducing some small scatterer into the medium itself. This method also increase the temporal separation between the ballistic and diffusive pulse after propagating through the medium and improve the quality of the image if the selection of ballistic part is made.

As noted above, a spatial filter will remove light which is scattered away from the collinear direction of the signal. In a highly scattering medium there is a substantial portion of multiple scattered light which, after passing through a random medium, travels in the same direction as the ballistic signal. This multiply scattered light exiting from the random medium in the same direction as the ballistic signal cannot be eliminated with a spatial filter. According to another feature of this invention, the introduction of an absorbing dye into a random medium can substantially reduce the noise arising from multiple scattered light with respect to the ballistic signal. The signal to noise ratio can be substantially increased by orders of a magnitude using this absorption approach.

Absorption can also be used to improve the capability of seeing through a random medium, including biological and medical medium by selecting a wavelength for the light which is stongly absorbed by the random medium.

The principle behind the absorption imaging approach is based on the fact that multiply scattered light undergoes random walk in the medium and thus travels over a longer path length than that of the ballistic signal. The distance the ballistic signal transverses through the slab of random medium is equal to the thickness of the slab. Light traveling over a longer path length has a higher probability of being attenuated. Thus, the introduction of a dye into a random medium will preferentially absorb the mulitple scattered light component over the ballistic portion.

When a plane ultrafast pulse is incident normally onto a slab of random medium with absorbing boundaries, the temporal profile of the scattered pulse exiting at a point on the opposite side of the slab predicted by the diffusion theory is $$I_s(t) = \frac{D}{\pi z^2} \sum_{m=1}^{\infty} m(\pi z/d)^2 \sin(m\pi z/d) e^{(-D(m\pi/d)^2)} e^{-vt/l_a} \quad (1)$$

where $D = vL_t/3$ is the diffusion coefficient, $d = z + 2z_0$, $z_0 = 0.71L_t$, V is the speed of photon, z is the thickness of the slab, $L_t$ is the transport mean free path, and $L_a$ is the absorption length. The total intensity of the diffuse light is obtained by integrating eq. (1) with respect to time from 0 to α. The amount is given by $$I_{total} = \frac{\sinh[3d^2(1 - z/d)/l_t l_a \pi]}{2\sinh[3d^2/l_t l_a \pi]} \quad (2)$$

Since the transmitted light is scattered in all directions, the intensity of the light scattered within a fraction of solid angle is given by $$I_{dts} = fI_{total} \quad (3)$$

On the other hand, the intensity of the ballistic signal transversing over distance z is reduced by $$I_c = e^{-z(1/l_t + 1/l_a)} \quad (4)$$

where $L_s$ is the photon scattering mean free path.

Figure 11:
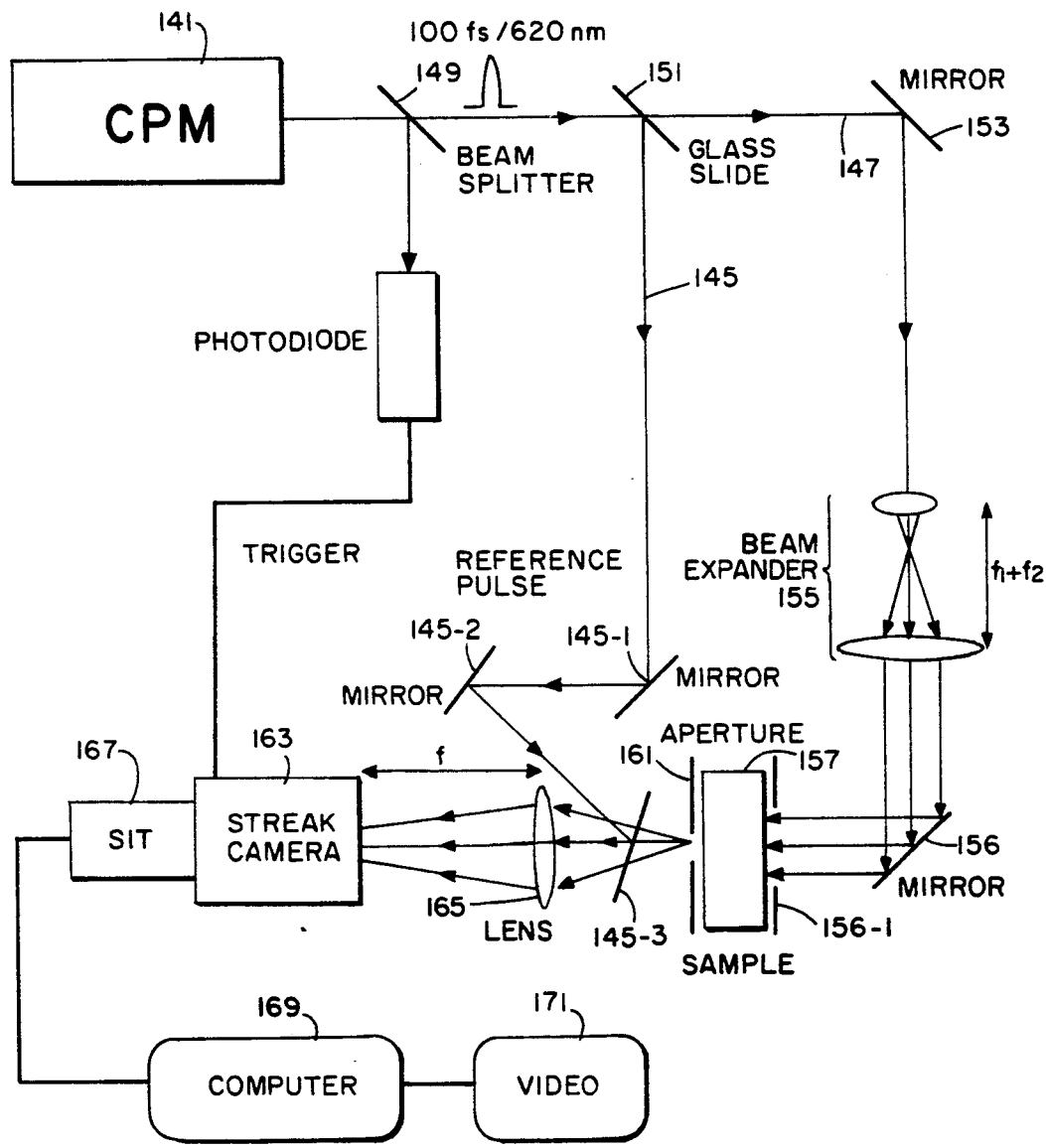
FIG. 11 is a schematic diagram of an experimental setup used for examining the absorption feature of the invention.

FIG. 11 shows the schematic of an experimental setup used to test the absorbtion feature of the invention. Ultrafast laser pulses of 80 fs were generated at a repetition rate of 82 MHz from a colliding pulse mode-locked dye laser system 141. The laser power was 5 mW and the laser wavelength was centered at 620 nm. The beam was split into three parts 143, 145 and 147 by a pair of beamsplitters 149 and 151. Part 147 was deflected off a mirror 153 and expanded from 4 mm to 35 mm beam diameter by an expander 155. The center portion of the expanded laser beam was deflected by a mirror 156 and incident through an aperture 156-1 on a random medium in a cylindrical glass cell 157 of 50 mm in diameter and 10 mm thick through an aperture 159. The random medium consisted of latex beads 10% concentration suspended in water and of 0.091 um diameter. Photons scattered out of the cell were lost. A black pinhole 161 of 2 mm diameter was placed at the center on the opposite side of cell 157. The temporal distribution of the photon exit from this pin hole in the forward direction within 4 mrad was measured by a synchroscan streak camera 163. A lens 165 imaged pin hole 161 onto the input slit of streak camera 163. The diameter of the incident beam was set to 20 mm (any further increase in the beam diameter will not change the pulse profile of the scattered photons.) Thus, the measured scattered pulse profile can be described by equation (1) when the thickness of the random medium is greater than 10 transport mean free path.

Beam part 145 was deflected off a pair of mirrors 145-1 and 145-2 off a beamsplitter 145-3 and used as a reference pulse. Beam part 143 was fed into a photodiode 167 which generated a trigger signal for streak camera 163.

The output of streak camera 163 is converted to electrical signals by SIT 167 which are fed into computer 169 for processing. The resulting image is displayed on video monitor 171.

Figure 12:
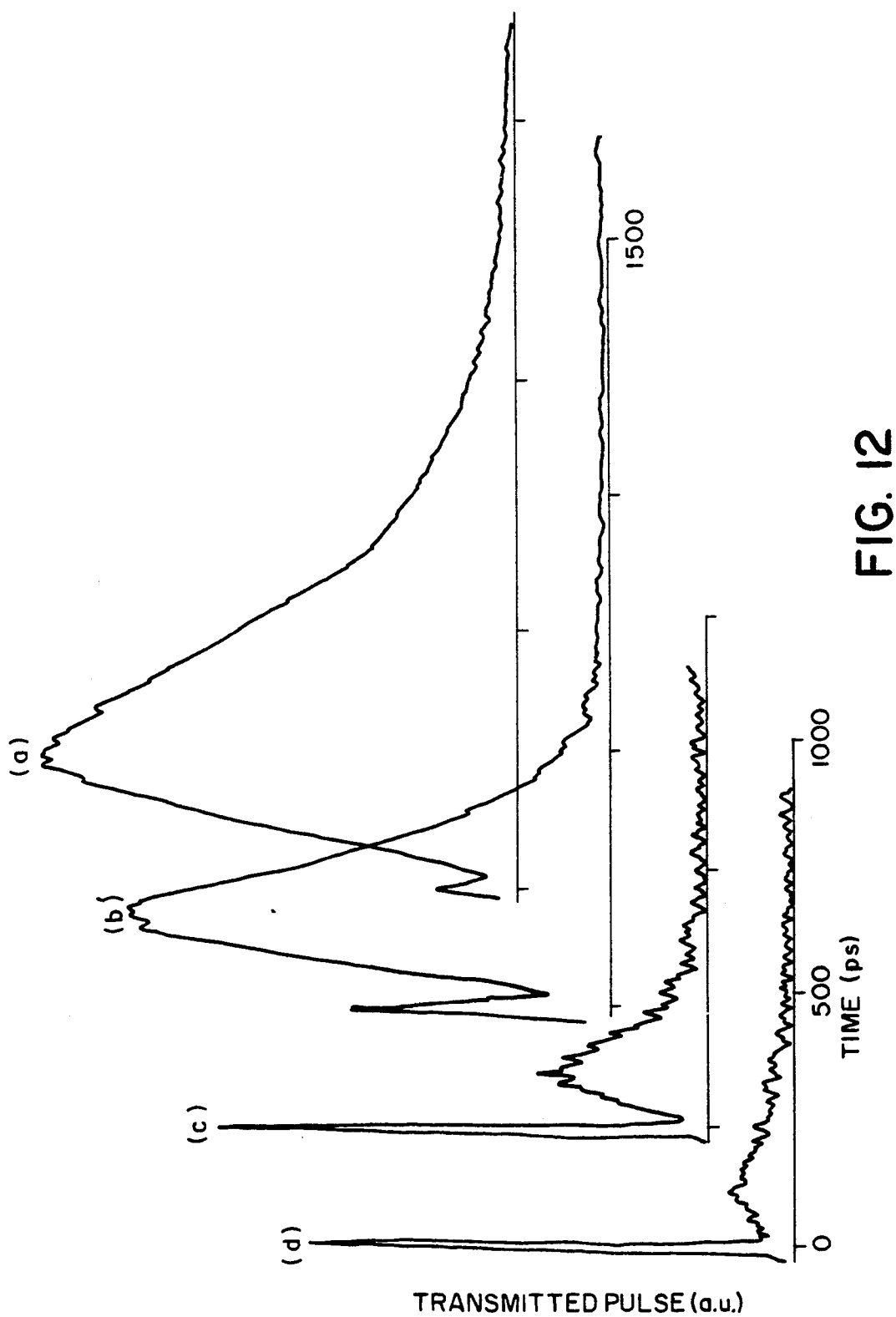
FIGS. 12(a) through (d) are graphs of transmitted pulse profiles through a slab of random medium of 10 mm thick with 10% concentration of latex beads of 0.091 $\mu$m diameter, at different absorbing dye concentrations; the absorption length of these media being (a) α, (b) 127, (c) 46 and (d) 21 mm.

The time resolved profiles of signal and diffuse light for different amounts of absorbing dye added into the random medium are presented in FIG. 12. The small peak at time 0 PSEC is the ballistc signal. This ballistic signal light arises from coherent interference amount the multiple scattered light traveling in the forward direction. The ballistic signal component is followed in time by a large temporal distribution of multiply scattered light. In FIG. 12(a) the total intensity of the diffuse light component is 130 times more than the intensity of the ballistic signal. It is not possible to see through such a cloudy medium. The photon transport mean free path was found to be 0.55 mm from fitting eq. (1) to the experimental result in curve (a) of FIG. 12. This random slab is $(z/l_t = 10 \text{ mm}/0.55 \text{ mm}) = 18$ transport mean free path thick.

FIGS. 12(b), (c) and (d) demonstrate several salient features. The transmitted pulse profiles change by increasing amount of absorbing dye in the random medium. The diffuse scattered light at later times which travel over a longer distances are attenuated more. The diffuse light intensity decreases more rapidly as more dye is added. The absorption lengths from these media were obtained experimentally by preparing the dye solutions (no beads in it). The transmission of the dye solutions were measured by a spectrophotometer. The percentage transmission of these dye solutions corresponding to curves (a), (b), (c), and (d) of FIG. 12 are 100, 92.5, 80.6 and 62.4% respectively. The corresponding absorption lengths are computed to be ∞, 127, 46, and 21 mm, respectively. FIG. 12(d) shows that the diffuse light intensity is substantially reduced with respect to signal intensity as compared with FIG. 12(a). In the case of FIG. 12(d) the total intensity of the diffuse light is equal to the intensity of the ballistic signal. The ballistic portion is enhanced over the diffuse portion.

Figure 13:
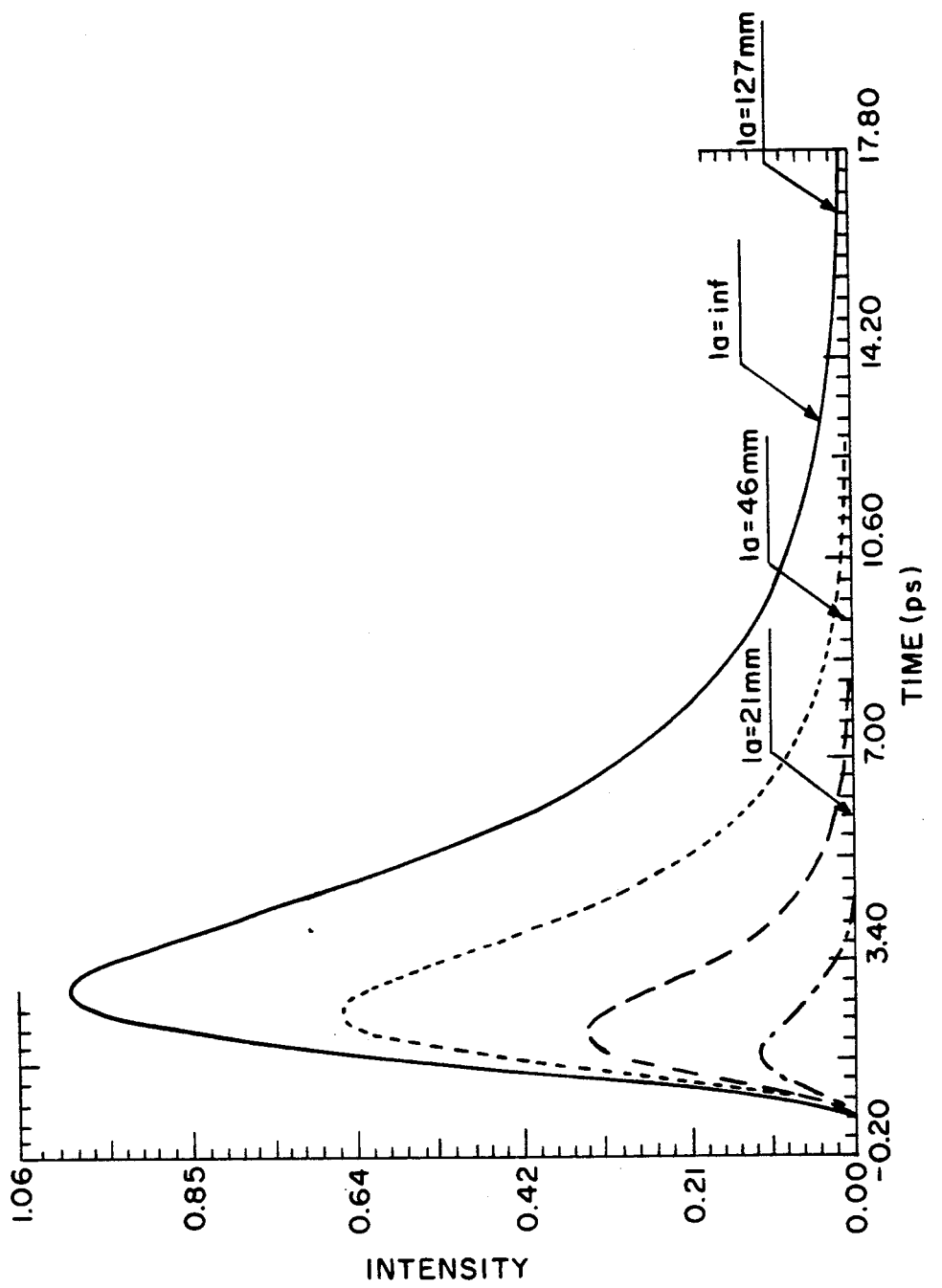
FIGS. 13(a) through (d) are theoretical plots of transmitted pulse profiles through a slab of random medium of 10 mm thick of transport mean free path of 0.55 mm; the absorption length of the media being: (a) α, (b) 127, (c) 46, (d) 21 mm.

A quantitative comparison between the diffuse and signal intensity is presented below. In a strongly scattering medium, the transmitted pulse of the diffuse component can be predicted by diffusion theory as in equation (1) by the transport means free path $L_t$ and the absorption length $L_a$. The absorption lengths decreses as more absorbing dye is added to the medium. FIG. 13 shows a theoretical plots of eq. (1) which correspond to the cases shown in FIG. 12 where the absoption lengths are α, 127, 46 and 21 mm. The intensity of diffuse light decreases rapidly especially for those photon arriving later in time. The photons are absorbed more by the dye added to the random medium.

Figure 14:
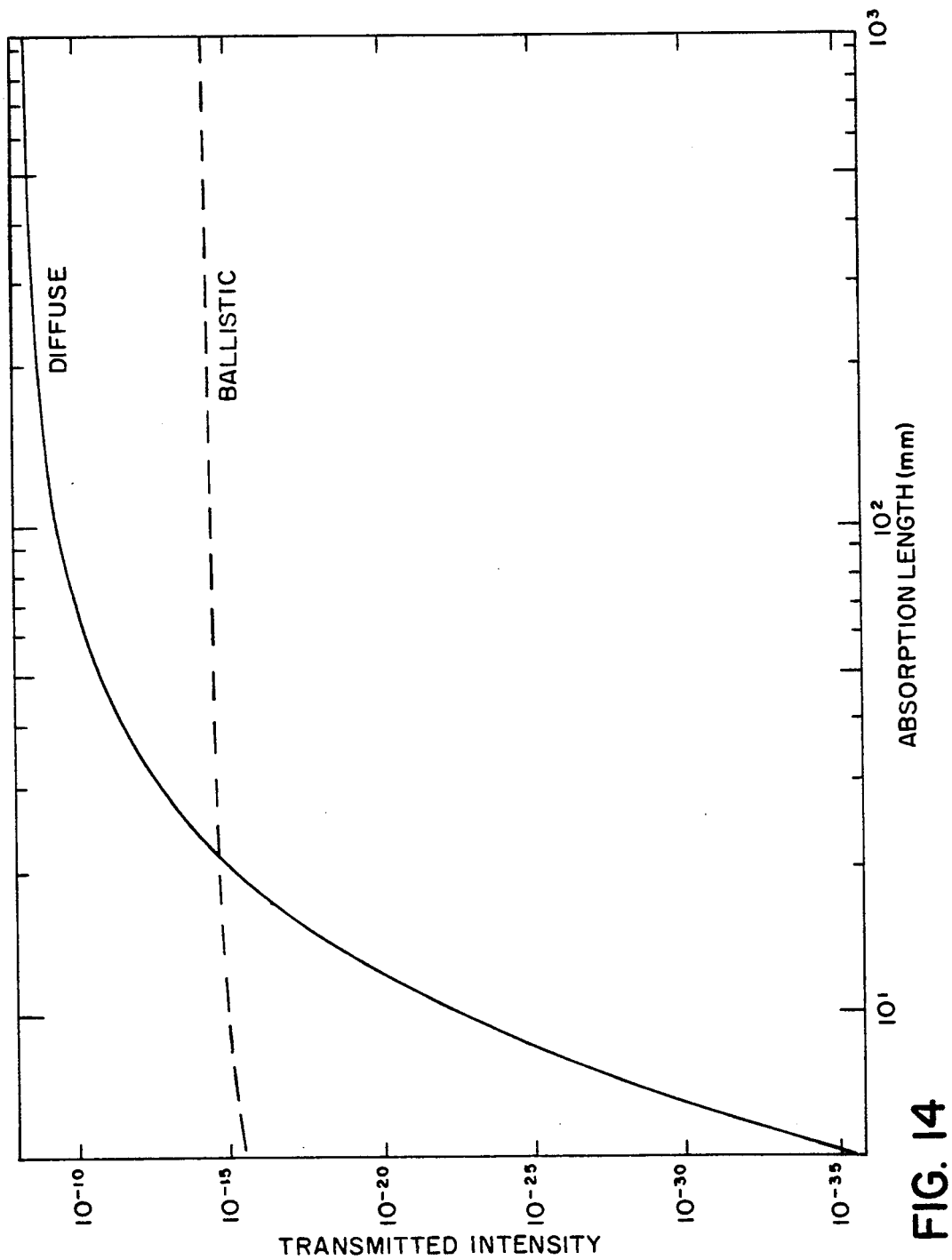
FIG. 14 is a graph of the theoretical prediction of the total diffuse light and signal intensity for media with different absorption lengths, using $f = 2 \times 10^{-4}$, and $l_t = 0.55$ mm.

In imaging of an object hidden inside a random medium using continuous wave laser, one is interested with the total (time integrated) intensity of the diffuse light compared with the intensity of the signal light. The total intensity of the diffuse light (noise) and signal are plotted in FIG. 14. As the absorption length decreases (increase in absorption), the intensity of the diffuse light decreases much faster than that of the signal light. The scattering parameters used are the transport mean free path = 0.55 mm and slab thickness z = 10 mm, which corresponds to the experimental results. The absorption lengths are varied from 1000 to 5 mm. In these limits, the diffuse intensity decreases from $7 \times 10^{-6}$ to $5 \times 10^{-21}$; and intensity drop by a factor of $10^{15}$. The corresponding intensity drops of the ballistic component decreases from $1\times10^{-8}$ to $1\times10^{-9}$, a drop of only by a factor of 10. There is a (ballistic) signal to (diffuse) noise ratio gain of a factor of $10^{14}$ when the absorption length changes from 1000 mm to 5 mm. This large amount of gain between ballistic signal and diffuse light can substantially increase the quality of image in highly scattering random media.

Figure 15:
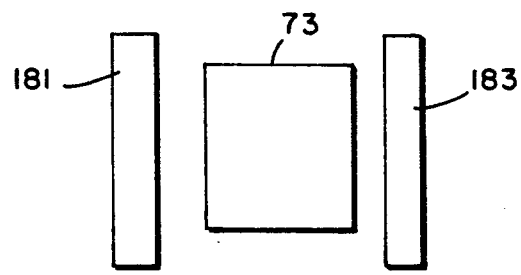
FIG. 15 illustrates another embodiment of the invention.

Thus, it can be seen that the diffuse noise can be substantially reduced with respect to ballistic signal through absorption in a random medium. This absorption, which reduces the noise with respect to signal is important to improve the quality of the image of an object hidden in a random or biomedical medium. In order to increase absorption, one can either choose a light wavelength which is absorbed by the biomedical medium or introduce an absorption dye into the medium or do both. Also, scattering can be reduced by adding a pair of parallel polarizers 181 and 183 as shown in FIG. 15.

Also, if the medium is made more random, the time separation between the ballistic and diffused light will be increased and as a result improve the signal to noise ratio in a time gating system. Furthermore, if the medium is made more ordered (i.e. less random) there will be less scattered light and hence a higher signal to noise ratio.

It should be noted that the illuminating radiation used in this invention is not limited to visible light, but rather can also be other forms of electromagnetic radiation such as radio waves, infrared radiation, ultraviolet radiation, x-rays and gamma rays.

The embodiments of the present invention is intended to be merely exemplary and those skilled in the art shall be able to make numerous variations and modifications to it without departing from the spirit of the present invention. All such variations and modifications are intended to be without the scope of the present invention as defined in the appended claims.

What is claimed is:

1. In an apparatus for imaging an object that is in or behind a semi-opaque random medium and which includes a radiation source for irradiating said object through said medium and a time gated detector for receiving radiation from the medium, the radiation received by the detector including scattered radiation and unscattered radiation, the scattered radiation being temporally separate from the unscattered radiation, the improvement comprising means for increasing the time separation between radiation from said medium which is scattered and radiation which is unscattered.

2. The apparatus of claim 1 and wherein the means for increasing the time separation comprises a quantity of semi-opaque random medium.

3. The apparatus of claim 1 and wherein the means for increasing the time separation comprises a quantity of scatterers in the semi-opaque random medium.

4. The apparatus of claim 1 and further including an absorbing dye for improving the quality of the radiation received by the detector and absorbing dye being in said semi-opaque random medium.

5. The apparatus of claim 1 and wherein the radiation source provides radiation of a wavelength or wavelengths in the absorption spectrum of the semi-opaque random medium.

6. A system for imaging an object hidden in or behind a semi-opaque random medium comprising:
(a) a light source for illuminating the object;
(b) means for spatially filtering the light from the object; and
(c) a streak camera for detecting light from the object and temporally gating said light; and
(d) a computer system for processing and recording the output of the streak camera.

7. An apparatus for forming an image of an object that is in or behind a semi-opaque random medium comprising:
(a) means for illuminating said object through said semi-opaque random medium with a beam of radiation,
(b) a streak camera for detecting radiation from said object and forming an image thereof said streak camera temporally gating the radiation received from said object
(c) a noise filter in front of the streak camera, and
(d) a space gate in front of the streak camera for spatially gating the light from the object.

8. The apparatus of claim 7 and further including a collector for collecting radiation from said semi-opaque random medium and directing said radiation into said detector.

9. A method of forming an image of an object that is in or behind a semi-opaque random medium comprising the steps of:
(a) illuminating said object through said semi-opaque random media with a beam of radiation,
(b) spatially gating the radiation from the object, and
(c) forming an image of said object using said spatially gated radiation and a streak camera.

10. An apparatus for forming an image of an object that is in or behind a semi-opaque random medium comprising:
(a) a light source and a first optical fiber for illuminating said object through said semi-opaque random medium with a beam of radiation,
(b) a detector for detecting radiation from said object and forming an image thereof, said detector being a time gated type detector so as to temporally gate the radiation received from said object,
(c) a noise filter in front of said detector, and
(d) a second optical fiber for collecting light from said object and directing said light into said detector.

11. The apparatus of claim 10 and wherein said detector is a streak camera.

12. The apparatus of claim 11 and further including an SIT camera for recording the output of the streak camera.

13. An apparatus for forming an image of an object that is in or behind a semi-opaque random medium comprising:
(a) means for illuminating said object through said semi-opaque random medium with a beam of radiation,
(b) a detector for detecting radiation from said object and forming an image thereof, said detector being a time gated type detector so as to temporally gate the radiation received from said object,
(c) a collector movable relative to said semi-opaque random medium for collecting radiation from semi-opaque random medium and directing said radiation into said detector.

14. The apparatus of claim 13 and further including a controller for synchronizing the positions of illumination and collection.

* * * * *